(12) United States Patent
Sasayama et al.

(10) Patent No.: US 7,289,597 B2
(45) Date of Patent: Oct. 30, 2007

(54) OPTICAL AXIS ADJUSTING MECHANISM FOR X-RAY LENS, X-RAY ANALYTICAL INSTRUMENT, AND METHOD OF ADJUSTING OPTICAL AXIS OF X-RAY LENS

(75) Inventors: Norio Sasayama, Chiba (JP); Akikazu Okawara, Chiba (JP); Satoshi Nakayama, Chiba (JP)

(73) Assignee: SII NanoTechnology Inc. (JP)

( * ) Notice: Subject to any disclaimer, the term of this patent is extended or adjusted under 35 U.S.C. 154(b) by 25 days.

(21) Appl. No.: 11/389,447

(22) Filed: Mar. 24, 2006

(65) Prior Publication Data
US 2006/0226340 A1    Oct. 12, 2006

(30) Foreign Application Priority Data
Apr. 12, 2005  (JP) .............................. 2005-114513

(51) Int. Cl.
*G21K 7/00* (2006.01)
(52) U.S. Cl. ...................................................... 378/43
(58) Field of Classification Search .................. 378/43, 378/44, 145, 204–206; 250/306, 307, 311, 250/201.3, 397; 359/368, 382, 510; 356/445
See application file for complete search history.

(56) References Cited
U.S. PATENT DOCUMENTS 2,951,157 A * 8/1960 Mulvey et al. ............. 250/310
5,351,279 A * 9/1994 She et al. ...................... 378/43
5,880,467 A * 3/1999 Martinis et al. ............. 250/310
6,839,405 B2 * 1/2005 Bani-Hashemi et al. ...... 378/65
7,072,442 B1 * 7/2006 Janik ............................ 378/84
2004/0005026 A1 * 1/2004 Fujii et al. ..................... 378/43

FOREIGN PATENT DOCUMENTS

JP        2003004676 A  *  1/2003

* cited by examiner

*Primary Examiner*—Edward J Glick
*Assistant Examiner*—Irakli Kiknadze
(74) *Attorney, Agent, or Firm*—Adams & Wilks

(57) ABSTRACT

An optical axis adjusting mechanism for an X-ray lens, an X-ray analytical instrument and a method of adjusting an optical axis of an X-ray lens, capable of enhancing detection efficiency of an X-ray while preventing degradation of the device performance are provided. An optical axis adjusting mechanism for an X-ray lens to be implemented in an X-ray analytical instrument, includes an exit side adjusting mechanism for adjusting an exit side focal point of the X-ray lens to focus on an X-ray detector, and an entrance side adjusting mechanism for adjusting an entrance side focal point of the X-ray lens to focus on an analytical point of a sample, and the entrance side adjusting mechanism is disposed with a greater distance from the X-ray lens than a distance between the exit side adjusting mechanism and the X-ray lens.

19 Claims, 14 Drawing Sheets

OPTICAL AXIS ADJUSTING MECHANISM FOR X-RAY LENS, X-RAY ANALYTICAL INSTRUMENT, AND METHOD OF ADJUSTING OPTICAL AXIS OF X-RAY LENS

BACKGROUND OF THE INVENTION

1. Field of the Invention

The present invention relates to an optical axis adjusting mechanism for X-ray lens for adjusting an optical axis of an X-ray lens implemented in an X-ray analytical instrument, an X-ray analytical instrument, and a method of adjusting an optical axis of an X-ray lens.

2. Description of the Related Art

In recent years, an X-ray analytical instrument for detecting an X-ray emitted from a sample in response to electron beam irradiation on the sample has been known to the public. A superconducting X-ray detector is preferably used as the X-ray analytical instrument of this kind because it dramatically enhances the energy resolution from the conventional level.

Incidentally, since the traveling directions of the emitted X-rays are individually different, it is desirable to enlarge the area of a receiver section of the detector in order for enhancing the receiving efficiency of the detector.

However, in order for enhancing the energy resolution of the detector, the X-ray detector, in particular the superconducting X-ray detector has no other choice than reducing the area of the receiver section. As a result, the detection efficiency of the X-rays emitted from the sample decreases. To cope with the above, the use of an X-ray lens is thought to be effective for enhancing the detection efficiency, and a method of applying a multispindle goniometer to optical axis adjustment is reported (See Giorgio Cappuccio et. al., "Capillary optics as an X-ray condensing lens: An alignment procedure" Kumakhov optics and application: selected research papers on Kumakhov optics and application 1998-2000 Edited by Muradin A. Kumakhov. Bellingham, Wash., USA: SPIE, c2000).

In the method of adjusting the optical axis while mounting the X-ray lens on the multispindle goniometer, however, it is difficult to dispose a sample, a sample stage, an excitation source such as an electron gun or an X-ray source, a superconducting X-ray detector, and other analytical detectors in a limited space, and accordingly, the detectors need to be set apart from the sample, thus problematically degrading the device performance.

SUMMARY OF THE INVENTION

Therefore, an object of the invention is to provide an optical axis adjusting mechanism for an X-ray lens, an X-ray analytical instrument and a method of adjusting an optical axis of an X-ray lens, capable of enhancing detection efficiency of an X-ray while preventing degradation of the device performance.

An optical axis adjusting mechanism according to an aspect of the invention includes an exit side adjusting mechanism for adjusting an exit side focal point of the X-ray lens to focus on an X-ray detector, and an entrance side adjusting mechanism for adjusting an entrance side focal point of the X-ray lens to focus on an analytical point of a sample, and the entrance side adjusting mechanism is disposed with a greater distance from the X-ray lens than a distance between the exit side adjusting mechanism and the X-ray lens.

According to this aspect of the invention, firstly the exit side focal point of the lens is adjusted by the exit side adjusting mechanism to focus on the X-ray detector, and by adjusting the entrance side focal point to focus on the analytical point of the sample by the entrance side adjusting mechanism in this state, the X-ray emitted from the sample and then collected by the X-ray lens can be detected by the detector, thus the detection efficiency can be enhanced. And further, since the entrance side adjusting mechanism is disposed with a greater distance from the X-ray lens than the distance between the exit side adjusting mechanism and the X-ray lens, the entrance side adjusting mechanism can be operated for focusing on the sample without disturbing the X-ray analytical instrument, thus enhancing workability. And, according to this aspect of the invention, since the space necessary for focusing on the sample can be reduced, the analytical detectors such as the superconducting X-ray detector can be disposed in the limited space, thus the detection efficiency of the X-ray can be enhanced while preventing degradation of the device performance.

Further, the exit side adjusting mechanism preferably includes a mechanism capable of translating the X-ray lens in parallel with two directions perpendicular to the optical axis of the X-ray lens.

Thus, the focal point can be adjusted to focus on the X-ray detector by translating in parallel with two directions perpendicular to the optical axis of the X-ray lens in adjusting the exit side focal point.

Further, the exit side adjusting mechanism preferably includes a mechanism capable of rotationally moving the X-ray lens around two axes passing through the entrance side focal point of the X-ray lens and perpendicular to the optical axis of the X-ray lens.

By thus arranging the configuration, the exit side focal point position can be adjusted without changing the entrance side focal point position.

Further, the exit side adjusting mechanism preferably includes a detachable section configured to allow at least a portion operated by an operator to be detached.

Thus, the operator can execute the operation more easily in adjusting the exit side focal point to focus on the X-ray detector by executing the operation while the detachable section is attached. And, by removing the detachable section therefrom after adjusting the exit side focal point of the lens to focus on the X-ray detector, the exit side adjusting mechanism can be prevented from disturbing the adjustment by the entrance side adjusting mechanism for focusing the entrance side focal point on the analytical point of the sample, thus enhancing the workability.

Further, the X-ray lens is preferably equipped with a holding mechanism for keeping the X-ray lens in a position adjusted by the exit side adjusting mechanism.

Accordingly, the exit side focal point of the lens is firstly adjusted by the exit side adjusting mechanism, and then, while keeping the adjusted position with the holding mechanism, the entrance side focal point of the X-ray lens can be adjusted by the entrance side adjusting mechanism, thus enhancing the workability. Note that in the case that the exit side adjusting mechanism includes the detachable section, the entrance side focal point of the lens can be adjusted while the holding mechanism keeps the adjusted position of the exit side focal point of the lens and the detachable section is removed, thus the workability can further be enhanced.

Further, the X-ray detector is preferably a superconducting X-ray detector mounted on a refrigerator, the entrance side adjusting mechanism is preferably disposed adjacent to the refrigerator, and the exit side adjusting mechanism can preferably be moved integrally with the refrigerator.

Accordingly, by moving the exit side adjusting mechanism integrally with the refrigerator in adjusting the entrance side focal point of the X-ray lens by the entrance side adjusting mechanism to focus on the analytical point of the sample, the entrance side focal point of the lens can be adjusted while keeping the positional relationship between the exit side focal point and the detector, and keeping the temperature of the X-ray detector at a predetermined level by the refrigerator, thus the workability can be enhanced.

Further, the entrance side adjusting mechanism preferably includes a mechanism capable of translating the refrigerator in parallel with two directions traversing the optical axis of the X-ray lens. Namely, the configuration includes two kinds of parallel translations.

Accordingly, by translating the refrigerator in parallel with two directions traversing the optical axis of the X-ray glens in adjusting the entrance side focal point, the X-ray lens can be moved integrally with the refrigerator to focus on the analytical point of the sample. Therefore, in implementing the X-ray lens in the instrument on which the sample is mounted, there is no need to implement it in a condition in which the adjustment in the two directions traversing the optical axis has been executed previously, but it is enough to execute the adjustment of the X-ray lens by the entrance side adjusting mechanism after it is implemented. Thus, the requirement for the positional accuracy of the X-ray lens in implementation in the instrument on which the sample is mounted can be eased, thus enhancing the workability.

Further, it is preferable that the two directions are substantially perpendicular to the optical axis of the X-ray lens.

Accordingly, the movement of the X-ray lens in the optical axis direction in adjusting the entrance side focal point can be suppressed, thus the risk of defocus in the optical axis direction can be avoided. Thus, the adjustable range of the parallel translation can be extended to ease the requirement for the positional accuracy of the X-ray lens in implementing the X-ray lens in the instrument on which the sample is mounted, thus enhancing the workability.

Further, the entrance side adjusting mechanism preferably includes a mechanism capable of translating the refrigerator in parallel with a horizontal direction perpendicular to the optical axis of the X-ray lens. Namely, the configuration includes one kind of parallel translation.

Accordingly, by translating the refrigerator in parallel with the horizontal direction substantially perpendicular to the optical axis of the X-ray lens in adjusting the entrance side focal point, the X-ray lens can be moved integrally with the refrigerator to focus on the analytical point of the sample. Therefore, in implementation in the instrument on which the sample is mounted, there is no need to implement it in a condition in which the adjustment in the translatable direction described above has been executed, but it is enough to execute the adjustment of the X-ray lens by the entrance side adjusting mechanism after it is implemented. Thus, the requirement for the positional accuracy of the X-ray lens in implementation in the instrument on which the sample is mounted can be eased, thus enhancing the workability. Note that in the case that a positional adjustment in the direction perpendicular to the translatable direction is necessary, the adjustment can be executed by changing the irradiation position of the excitation source taking a measure of, for example, changing the focal distance of the electron gun.

Further, the entrance side adjusting mechanism preferably includes a mechanism capable of rotationally moving the refrigerator around each of two axes positioned differently from the optical axis of the X-ray lens and passing through the refrigerator or an area adjacent to the refrigerator. Namely, the configuration includes two kinds of rotational movements.

Accordingly, by rotationally moving the refrigerator around each of two axes positioned differently from the optical axis of the X-ray lens and passing through the refrigerator or an are adjacent to the refrigerator in adjusting the entrance side focal point, the X-ray lens can be moved integrally with the refrigerator to focus on the analytical point of the sample. Therefore, in implementing the X-ray lens in the instrument on which the sample is mounted, there is no need to implement it in a condition in which the positional adjustment of the X-ray lens in the rotationally movable direction described above has been executed previously, but it is enough to execute the adjustment of the X-ray lens by the entrance side adjusting mechanism after it is implemented. Thus, the requirement for the positional accuracy of the X-ray lens in implementing it in the instrument on which the sample is mounted can be eased, thus enhancing the workability.

Further, the entrance side adjusting mechanism preferably includes a mechanism capable of rotationally moving the refrigerator around a rotational axis positioned differently from the optical axis of the X-ray lens and passing through the refrigerator or an area adjacent to the refrigerator, and it is preferable that the rotational axis the mechanism rotationally moves the refrigerator around is substantially perpendicular to the ground. Namely, the configuration includes one kind of rotational movement.

Accordingly, by rotationally moving the refrigerator around the rotational axis in adjusting the entrance side focal point, the X-ray lens can be moved integrally with the refrigerator to focus on the analytical point of the sample. Therefore, in implementation in the instrument on which the sample is mounted, there is no need to implement it in a condition in which the positional adjustment of the X-ray lens in the movable direction in accordance with the rotational movement described above has been executed, but it is enough to execute the adjustment of the X-ray lens by the entrance side adjusting mechanism after it is implemented. Thus, the requirement for the positional accuracy of the X-ray lens in implementation in the instrument on which the sample is mounted can be eased, thus enhancing the workability. Note that in the case that a positional adjustment in the direction perpendicular to the translatable direction is necessary, the adjustment can be executed by changing the irradiation position of the excitation source taking a measure of, for example, changing the focal distance of the electron gun.

Further, the entrance side adjusting mechanism preferably moves the entrance side focal point of the X-ray lens approximately parallel to a direction substantially perpendicular to the optical axis of the X-ray lens by the rotational movement around the rotational axis.

Accordingly, the movement of the X-ray lens in the optical axis direction in adjusting the entrance side focal point can be suppressed, thus the risk of defocus in the optical axis direction can be avoided. Thus, the adjustable range of the rotational movement can be extended to ease the requirement for the positional accuracy of the X-ray lens in implementing it in the instrument on which the sample is mounted, thus enhancing the workability.

Further, the entrance side adjusting mechanism preferably includes a mechanism capable of moving the entrance side focal point of the X-ray lens integrally with the refrigerator in a horizontal direction.

Accordingly, by moving the refrigerator in the horizontal direction in adjusting the entrance side focal point, the X-ray lens can be moved in the horizontal direction integrally with the refrigerator to focus on the analytical point of the sample. Therefore, in implementation in the instrument on which the sample is mounted, there is no need to implement it in a condition in which the positional adjustment of the X-ray lens in the horizontal direction has been executed previously, but it is enough to execute the adjustment of the X-ray lens by the entrance side adjusting mechanism after it is implemented. Thus, the requirement for the positional accuracy of the X-ray lens in implementation in the instrument for adjusting the entrance side focal point can be eased, thus enhancing the workability.

Further, the entrance side adjusting mechanism preferably includes a mechanism capable of translating the entrance side focal point of the X-ray lens integrally with the refrigerator in parallel with a direction traversing the optical axis of the X-ray lens, and a mechanism capable of rotationally moving the entrance side focal point of the X-ray lens integrally with the refrigerator around an axis positioned differently from the optical axis of the X-ray lens. Namely, the configuration includes one kind of parallel translation and one kind of rotational movement.

Accordingly, by translating in parallel and rotationally moving the refrigerator with respect to the axes having the relationship described above with the optical axis in adjusting the entrance side focal point, the X-ray lens can be moved integrally with the refrigerator to focus on the analytical point of the sample. Therefore, in implementation in the instrument on which the sample is mounted, there is no need to implement it in a condition in which the adjustment in the parallel translatable direction and the rotationally movable direction described above has been executed, but it is enough to execute the adjustment of the X-ray lens by the entrance side adjusting mechanism after it is implemented. Thus, the requirement for the positional accuracy of the X-ray lens in implementing in the instrument on which the sample is mounted can be eased, thus enhancing the workability.

Further, the entrance side adjusting mechanism is preferably capable of adjusting the entrance side focal point of the X-ray lens, while firmly connecting a stage mounting the entrance side adjusting mechanism to an analytical vessel containing the sample, an excitation source and a detector, and then inserting the X-ray lens in the analytical vessel.

Accordingly, the entrance side focal point of the X-ray lens can be adjusted by adjusting the position of the refrigerator by the entrance side adjusting mechanism while the stage is firmly connected to the analytical vessel, thus the workability can be enhanced.

Further, the entrance side adjusting mechanism is preferably capable of adjusting the entrance side focal point of the X-ray lens, while connecting the refrigerator to a scanning electron microscope via a bellows, and firmly connecting a stage mounting the entrance side adjusting mechanism to the scanning electron microscope, and then inserting the X-ray lens in a vacuum vessel of the scanning electron microscope.

Accordingly, the entrance side focal point of the X-ray lens can be adjusted by adjusting the position of the refrigerator by the entrance side adjusting mechanism while the stage is firmly connected to the scanning electron microscope, thus the workability can be enhanced.

Further, a method of adjusting an optical axis according to another aspect of the invention includes the step of disposing an entrance side adjusting mechanism for adjusting an entrance side focal point of the X-ray lens to focus on an analytical point of a sample with a greater distance from the X-ray lens than a distance between an exit side adjusting mechanism for adjusting an exit side focal point of the X-ray lens to focus on an X-ray detector and the X-ray lens, the step of adjusting, by the exit side adjusting mechanism, the exit side focal point of the X-ray lens to focus on the X-ray detector, and the step of adjusting, by the entrance side adjusting mechanism, the entrance side focal point of the X-ray lens to focus on the analytical point of the sample after adjusting the exit side focal point.

According to this aspect of the invention, the entrance side adjusting mechanism can be operated without disturbing the X-ray analytical instrument in focusing on the sample, thus the workability can be enhanced.

Further, an X-ray analytical instrument according to still another aspect of the invention includes the optical axis adjusting mechanism for an X-ray lens described above.

Accordingly, the entrance side adjusting mechanism can be operated without disturbing the X-ray analytical instrument in focusing on the sample, thus the workability can be enhanced.

According to the invention, the detection efficiency of an X-ray can be enhanced while preventing degradation in the performance of the instrument.

BRIEF DESCRIPTION OF THE DRAWINGS

The invention will now be described with reference to the accompanying drawings.

DESCRIPTION OF THE PREFERRED EMBODIMENTS

An optical axis adjusting mechanism for X-ray lens, an X-ray analytical device and a method of adjusting an optical axis of an X-ray lens according to each of embodiments of the invention will hereinafter be explained with reference to the accompanying drawings.

Figure 1:
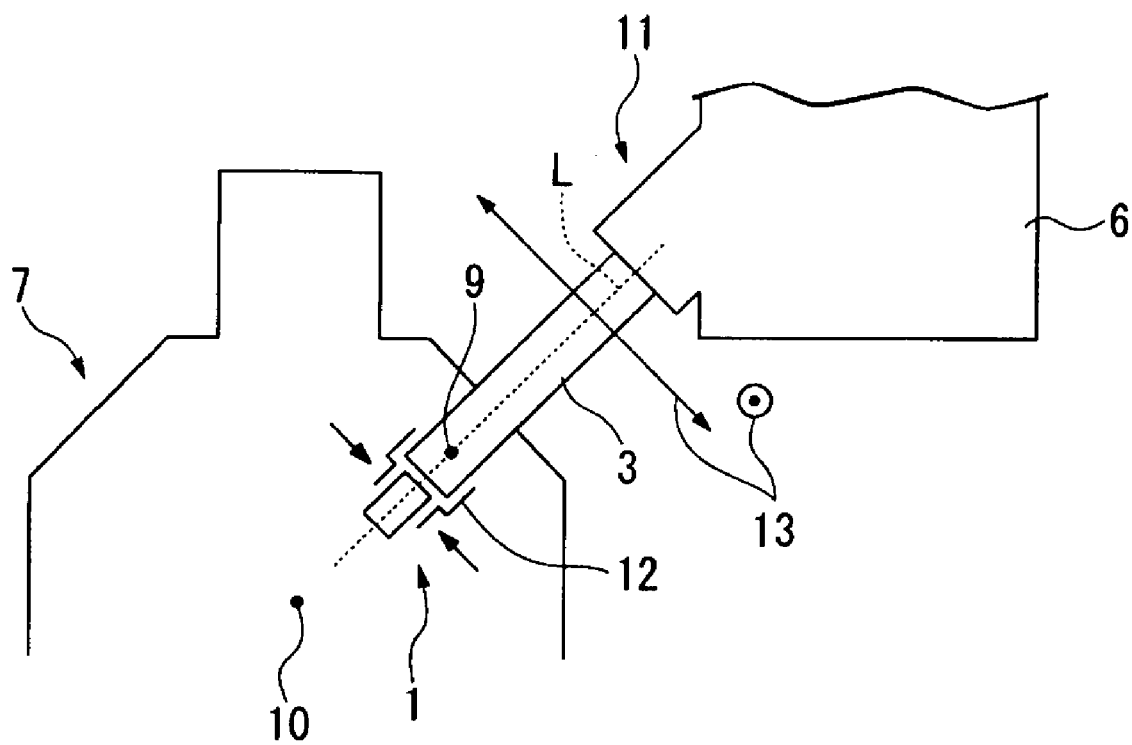
FIG. 1 is a schematic cross-sectional view of an X-ray analytical device equipped with an optical axis adjusting mechanism for an X-ray lens according to an embodiment of the invention.

FIG. 1 is a schematic cross-sectional view of an X-ray analytical device equipped with an optical axis adjusting mechanism for an X-ray lens according to an embodiment of the invention. As shown in the drawing, the X-ray analytical device 11 according to the present embodiment is used while being mounted in a scanning electron microscope (SEM for short) 7 for detecting X-rays emitted from a sample 10 held in the scanning electron microscope 7, thereby analyzing the sample.

The X-ray analytical device 11 has a configuration in which an X-ray lens 1 is mounted on the tip of a snout 3, which has an elongate cylindrical shape, to be inserted in the scanning electron microscope 7. The X-ray lens 1 is disposed so that the entrance side surface thereof faces the sample 10 held in the scanning electron microscope 7. Meanwhile, an X-ray detector 9 is disposed inside the snout 3 so as to face the exit side surface of the X-ray lens 1. A superconducting X-ray detector is used as the X-ray detector 9 in the present embodiment.

And, a refrigerator 6 is disposed in a base end side of the snout 3, and the superconducting X-ray detector 9 is refrigerated to a predetermined temperature near to the transition end by the refrigerator 6. The snout 3 is provided integrally with the refrigerator 6 in the present embodiment. Accordingly, the focal point of the entrance side (the sample 10 side) of the X-ray lens 1 mounted on the snout 3 can be adjusted by operating an entrance side adjusting mechanism (the specific configuration thereof will be described later with reference to FIGS. 9 through 18) 13 to move the refrigerator 6, and therefore the snout 3 integrally provided to the refrigerator 6, in two directions perpendicular to the optical axis L as illustrated with the arrows. Meanwhile, an exit side adjusting mechanism 12 is provided on a tip portion of the snout 3, and the focal point of the exit side (the detector 9 side) of the X-ray lens 1 can be adjusted by operating the exit side adjusting mechanism 12.

Figure 2:
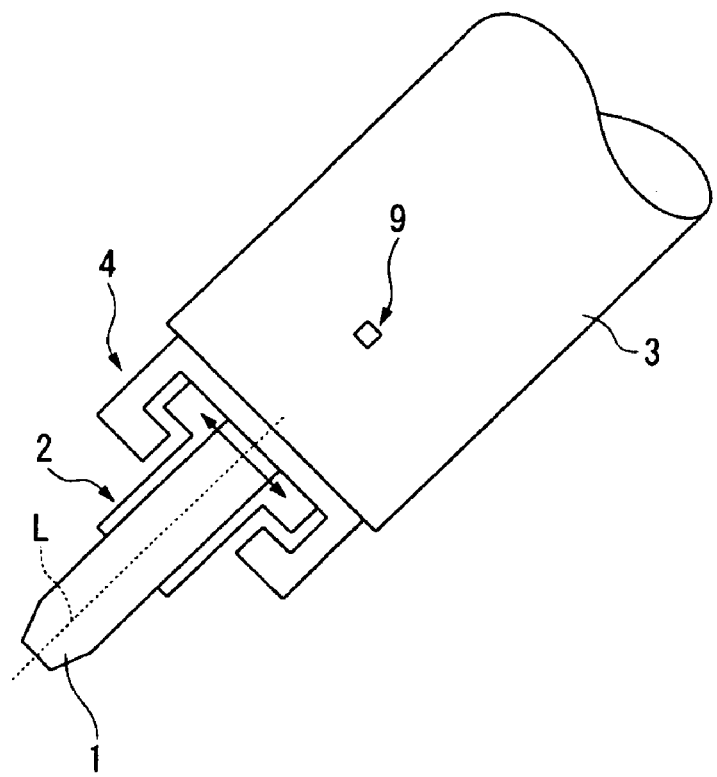
FIG. 2 is a schematic cross-sectional view of an exit side adjusting mechanism disposed on a tip portion of a snout.

FIG. 2 is a schematic cross-sectional view of the exit side adjusting mechanism provided on the tip portion of the snout. As shown in the drawing, the tip portion of the snout 3 is provided with a lens holder slide 4 capable of sliding a lens holder 2 for holding the X-ray lens 1 in a substantially perpendicular direction with respect to the optical axis L.

The exit side focal point of the X-ray lens 1 is adjusted to focus on the superconducting X-ray detector 9 by operating the lens holder slide 4.

Figure 3:
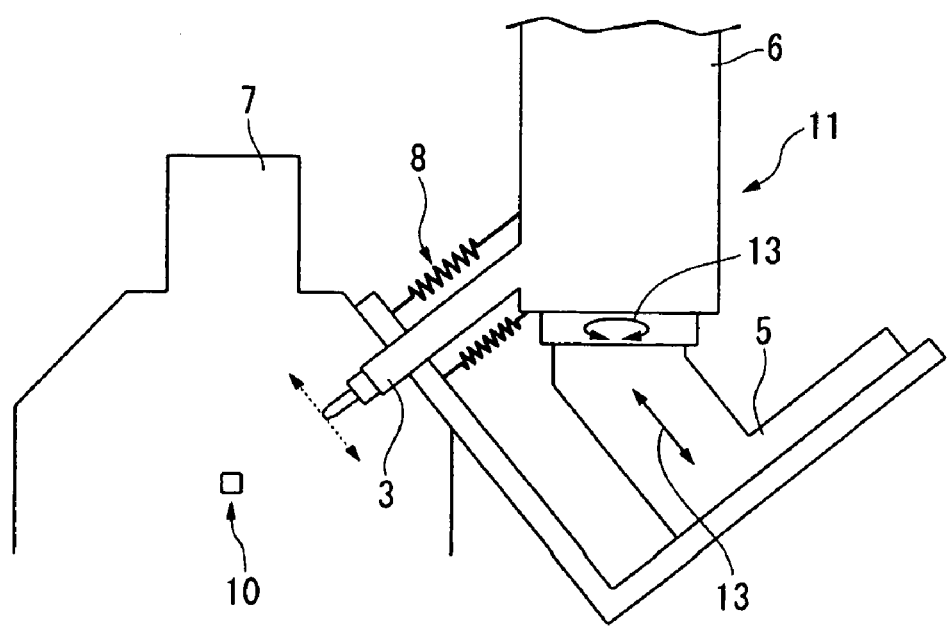
FIG. 3 is a schematic cross-sectional view of an entrance side adjusting mechanism disposed in a refrigerator side.

FIG. 3 is a schematic cross-sectional view of the entrance side adjusting mechanism disposed in the refrigerator side. As shown in the drawing, the X-ray analytical device 11 is adjusted, while the tip portion of the snout 3 is inserted in a vessel of the scanning electron microscope 7 holding the sample 10 inside, by the entrance side adjusting mechanism 13 mounted on the refrigerator 6 integrally coupled to the snout 3 so as to adjust the entrance side focal point of the X-ray lens 1 to focus on the sample 10. In this case, a bellows 8 is mounted between the vessel of the scanning electron microscope 7 and the refrigerator 6 and in the periphery of the snout 3, and the exit side focal point of the X-ray lens can be adjusted by moving the snout 3 integrally with the refrigerator 6 while maintaining the contact between the X-ray analytical device 11 and the scanning electron microscope 7 by the bellows 8.

Figure 4:
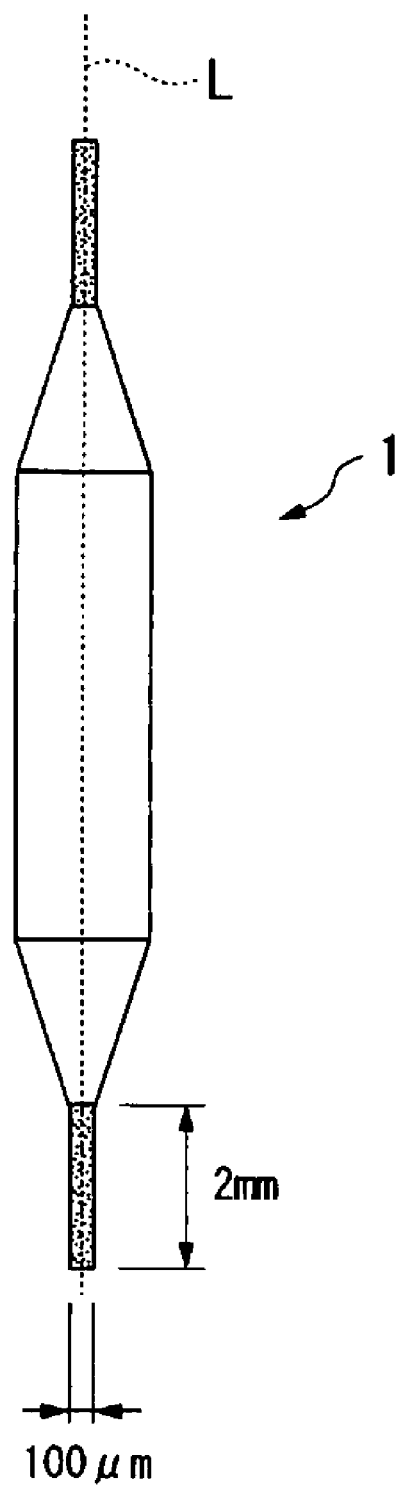
FIG. 4 is an explanatory diagram showing necessary accuracy in adjusting the focal point of an X-ray lens.

Now, the characteristics of the X-ray lens 1 will be explained with reference to FIG. 4. FIG. 4 is an explanatory diagram showing necessary accuracy in adjusting the focal points of the X-ray lens. As shown in the drawing, the X-ray lens 1 is formed to have focusing accuracy required in a direction along the optical axis L of 2 mm and focusing accuracy required in a direction perpendicular to the optical axis L of 100 nm. Namely, the X-ray lens 1 has characteristics requiring relatively low focusing accuracy in the direction along the optical axis L while requiring relatively high accuracy in the direction perpendicular to the optical axis L. Note that the numerical values shown in the drawing are examples only, and it is obvious that the focusing accuracy is not limited to the numeral values.

Figure 5:
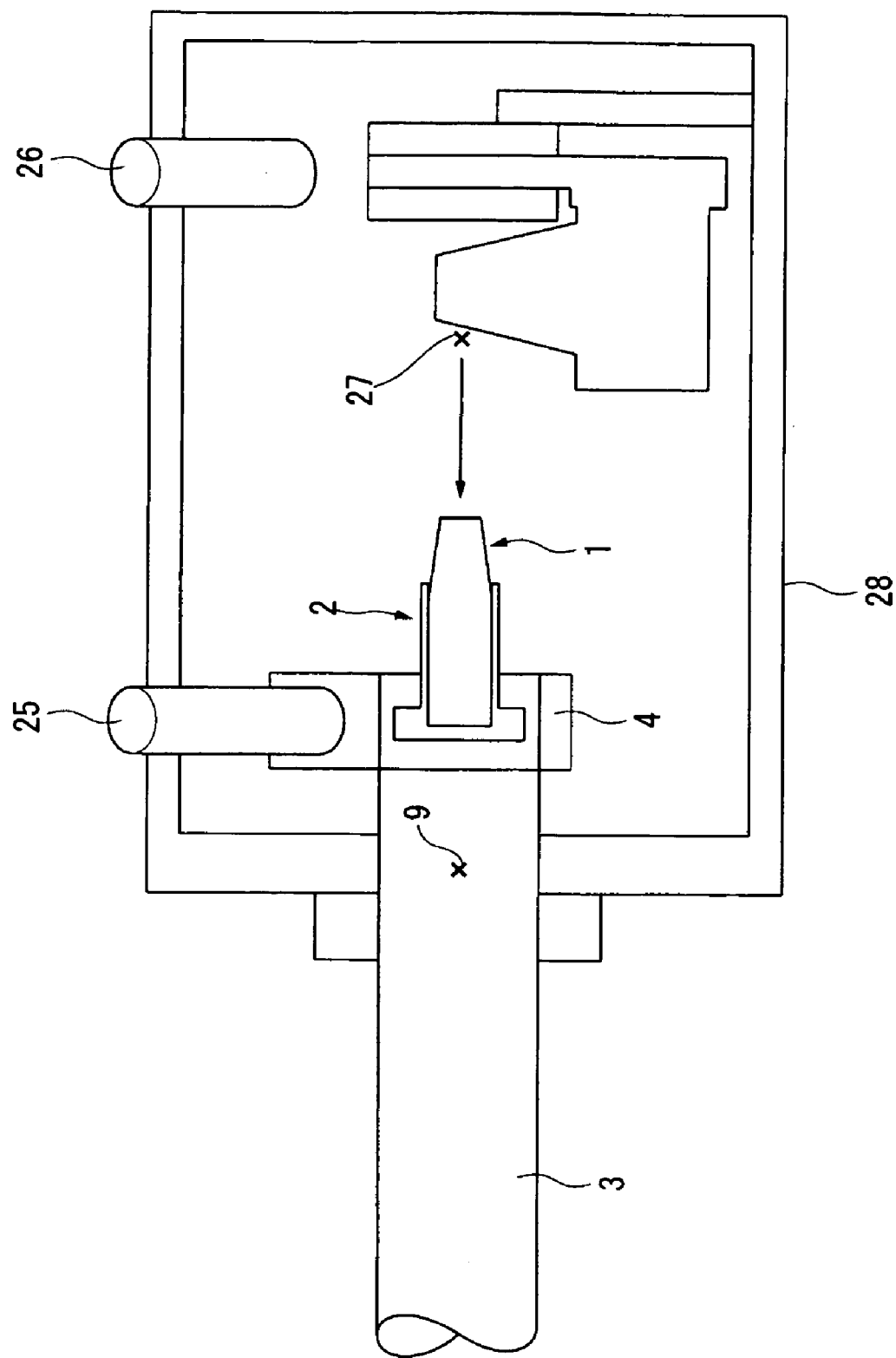
FIG. 5 is an explanatory view showing a condition of an exit side adjustment processing device with a snout mounted thereon.

FIG. 5 is an explanatory view showing a condition of an exit side adjustment processing device with the snout mounted thereon. As shown in the drawing, the exit side adjustment processing device is equipped with a vessel 28 formed substantially hollow and having a substantially rectangular cross-section, an X-ray source 27 mounted inside the vessel 28 for emitting an X-ray in a predetermined direction, and a micrometer 26 for adjusting the position of the X-ray source 27.

And, the exit side position of the X-ray lens 1 is adjusted by operating micrometers 25 mounted on the tip portion of the snout 3 to slide the lens holder 2 accommodating the X-ray lens 1 in a condition in which the tip portion of the snout 3 is inserted from an opening section (not shown) of the vessel 28.

Figure 6:
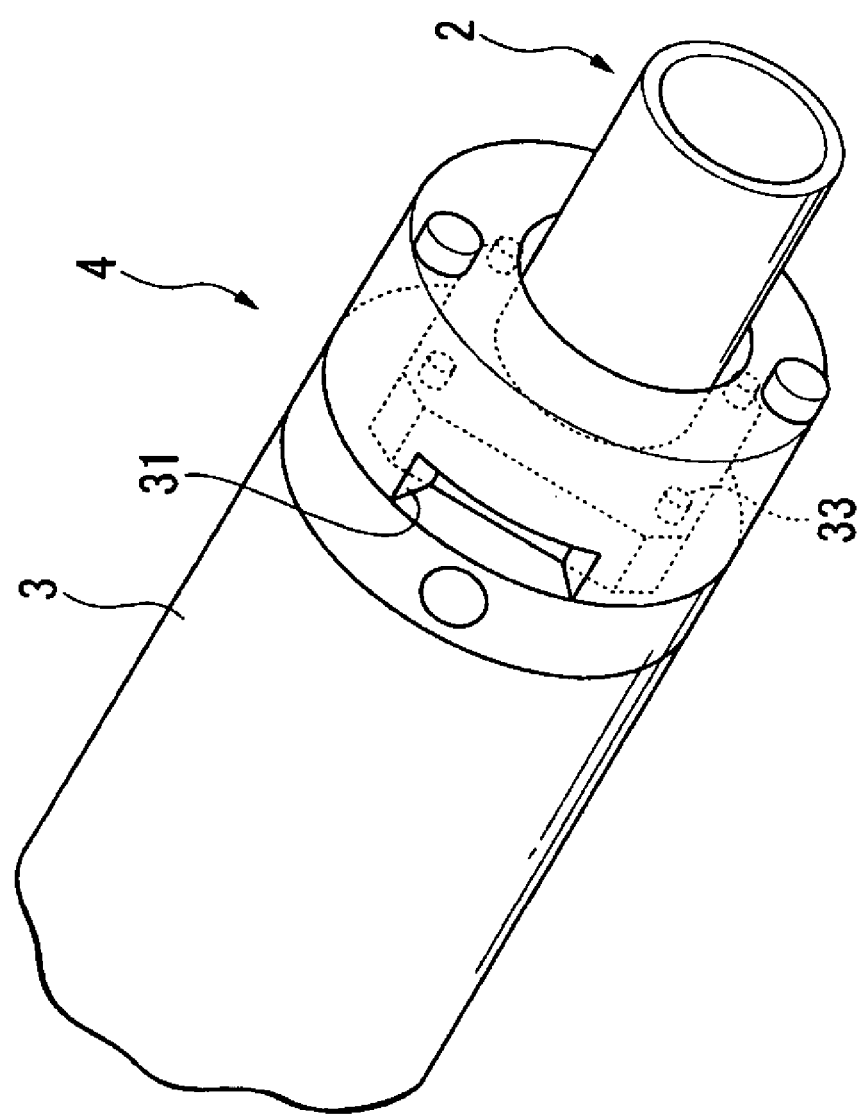
FIG. 6 is a perspective view showing a substantial part of an exit side adjusting mechanism disposed on a tip portion of a snout.

FIG. 6 is a cross-sectional view showing a substantial part of the exit side adjusting mechanism provided on the tip portion of the snout. As shown in the drawing, the lens holder slide 4 is provided with slots 31 for inserting the micrometers 25 formed in the circumferential surface thereof.

Figure 7:
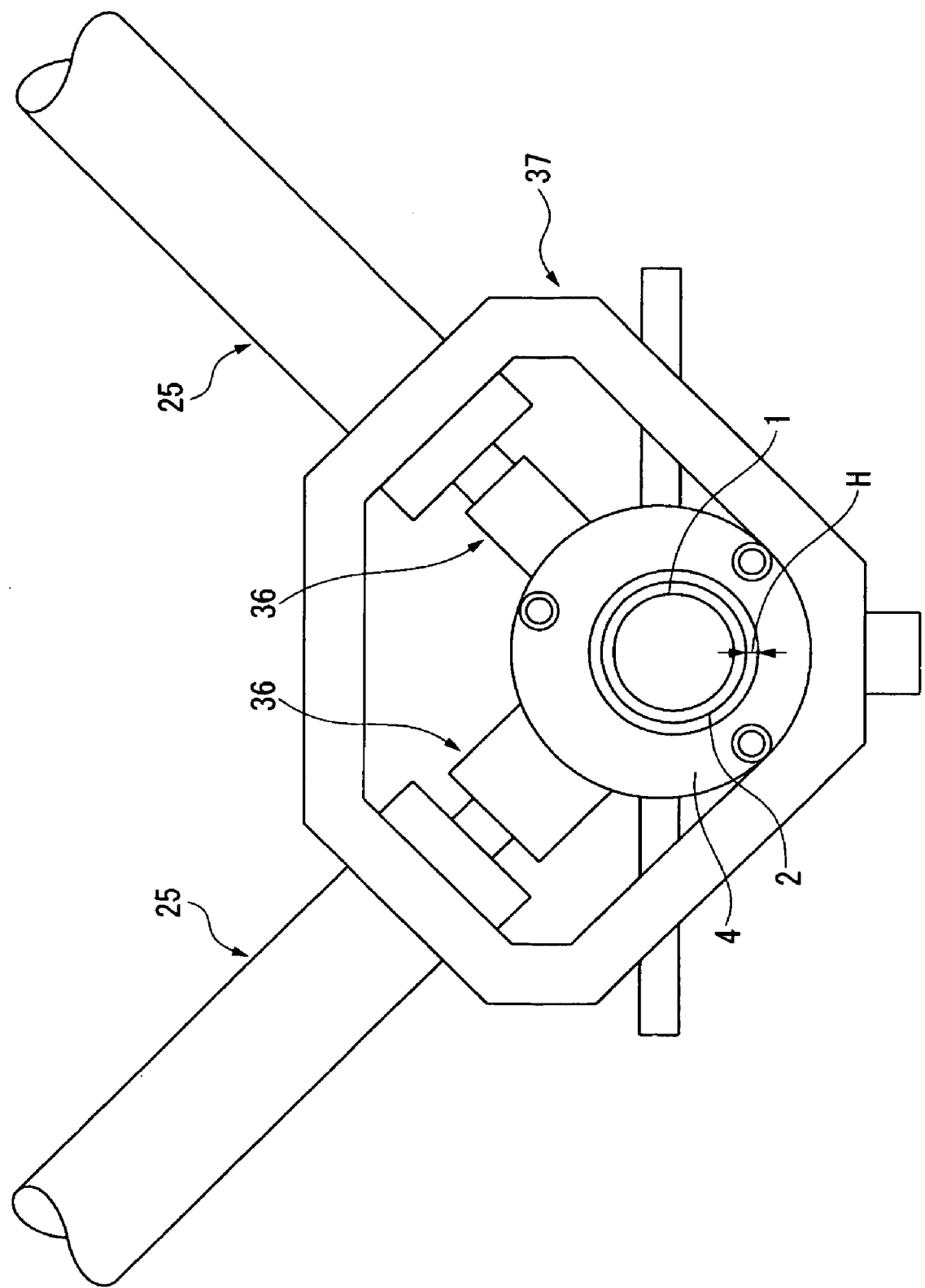
FIG. 7 is a plan view showing an exit side adjusting mechanism.

FIG. 7 is a plan view showing the exit side adjusting mechanism. As shown in the drawing, the micrometers 25 are implemented to the inserting slots 31 at the tip end part of the snout 3, and an operator operates the micrometers 25 to execute the exit side adjustment of the X-ray lens 1. Further, a frame 37 for holding the micrometers 25 is disposed in the periphery of the snout 3. As described above, the micrometers 25 to be operated by the operator are arranged to be detachable from the snout 3.

Figure 8:
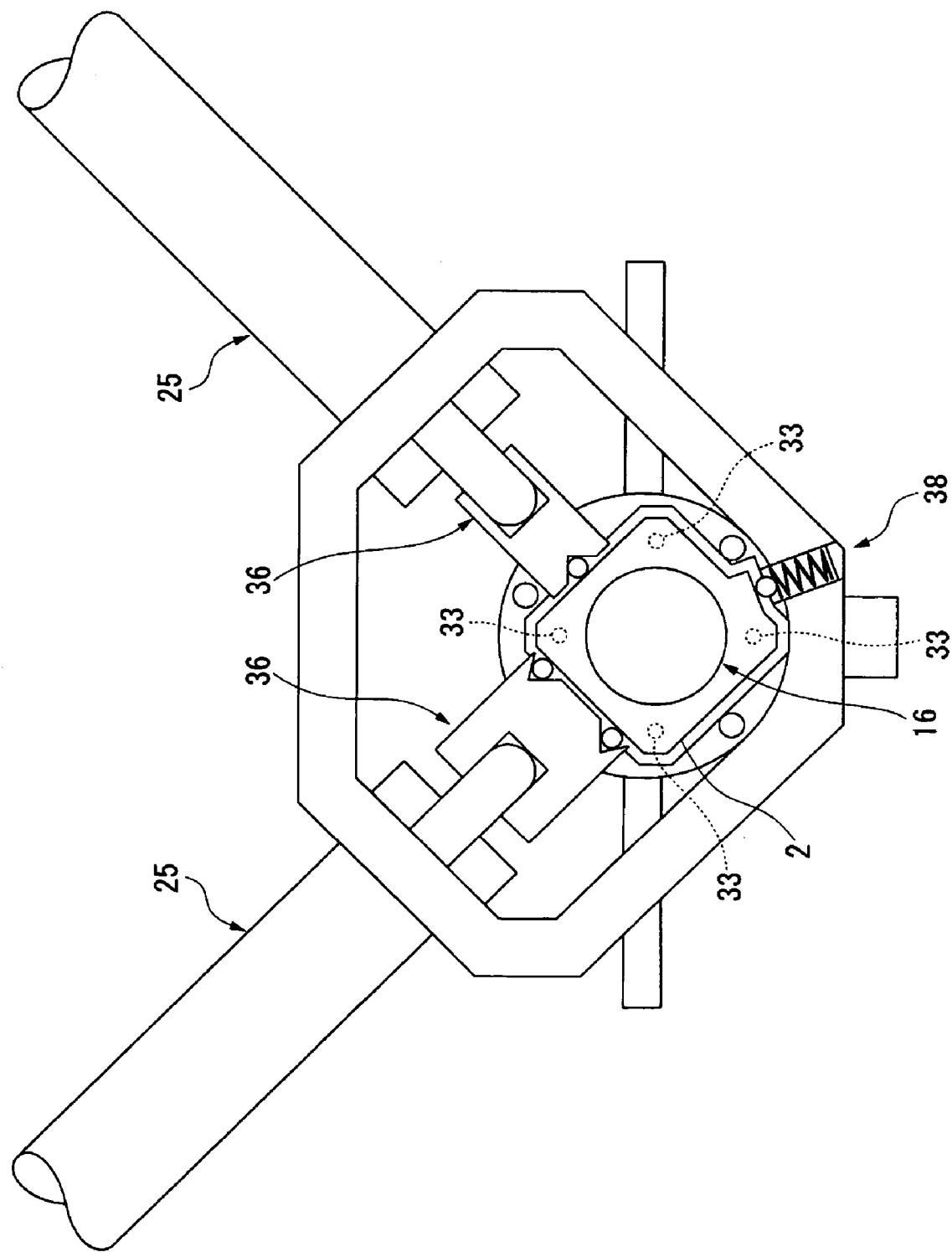
FIG. 8 is a cross-sectional view showing an internal structure of the exit side adjusting mechanism shown in FIG. 7.

FIG. 8 is a cross-sectional view showing an internal structure of the exit side adjusting mechanism shown in FIG. 7. As shown in the drawing, pressing components 36 for holding the lens holder slide 4 with pressure are mounted on tip portions of the micrometers 25 and inside the frame 37. The positions of the pressing components 36 can be shifted alternatively near to and apart from the lens holder slide 4 by rotating the respective micrometers 25 in forward and backward directions, respectively. Further, the frame 37 has a pushing spring 38 built-in for biasing the lens holder slide 4 in a direction for abutting on the pressing components 36. Therefore, the position of the lens holder slide 4 can be controlled by operating the micrometers 25 to shift the positions of the pressing components 36, thereby adjusting the exit side focal point of the X-ray lens 1 held in the lens holder slide 4. Further, holding screws 33 are provided for keeping the position of the lens holder slide 4.

Figure 9:
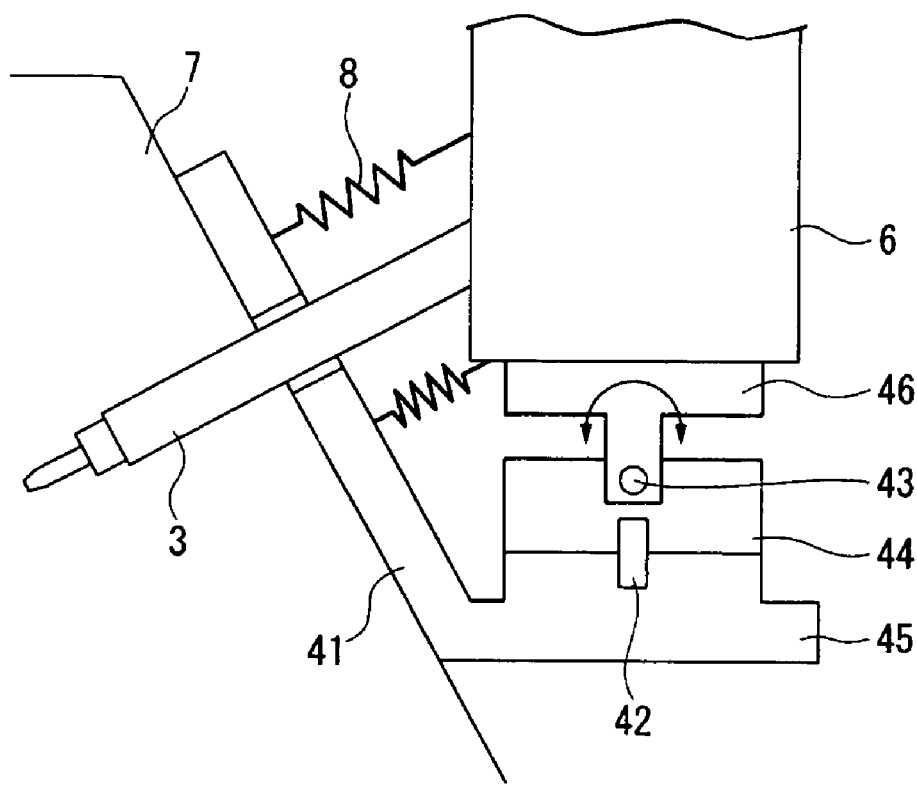
FIG. 9 is a schematic cross-sectional view showing a rough outline of an entrance side adjusting mechanism.
Figure 10:
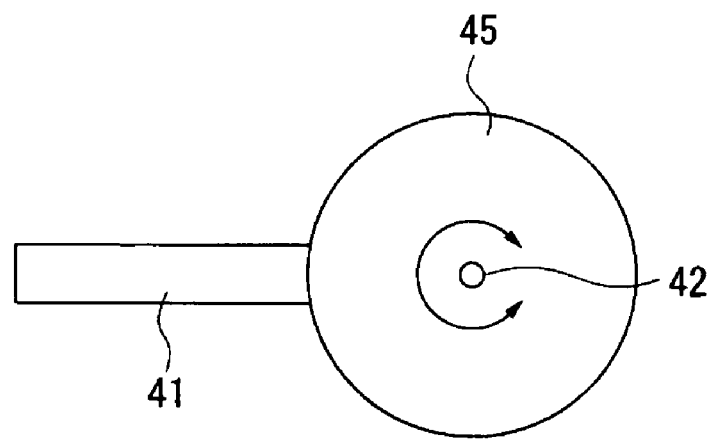
FIG. 10 is a schematic plan view of the entrance side adjusting mechanism shown in FIG. 9.

FIG. 9 is a schematic cross-sectional view showing a rough outline of the entrance side adjusting mechanism. FIG. 10 is a schematic plan view of the entrance side adjusting mechanism shown in FIG. 9. As shown in FIG. 9, a refrigerator supporting member 46 mounted on the lower surface of the refrigerator 6 and a receiving section 45 of a bracket 41 fixed to the vessel of the scanning electron microscope 7 along the side surface thereof are connected with each other via a turntable member 44. The turntable member 44 is rotatably mounted on the receiving section 45 via a spindle 42 provided in a center portion of the turntable member 44. Thus, the turntable member 44 can rotate with respect to the receiving section 45 alternatively in forward and backward directions, accompanied by the refrigerator 6 coupled to the turntable member 44 rotating around the spindle 42 (See FIG. 10). Further, the supporting member 46 is pivotally mounted on the turntable member 44 via a rotary shaft 43. Thus, the refrigerator 6 coupled to the supporting member 46 can be pivoted around the rotary shaft 43. By thus rotationally moving the refrigerator 6, the snout 3 integrally coupled to the refrigerator 6 and further the entrance side focal point of the X-ray lens 1 mounted on the tip potion of the snout 3 can be adjusted.

Figure 11:
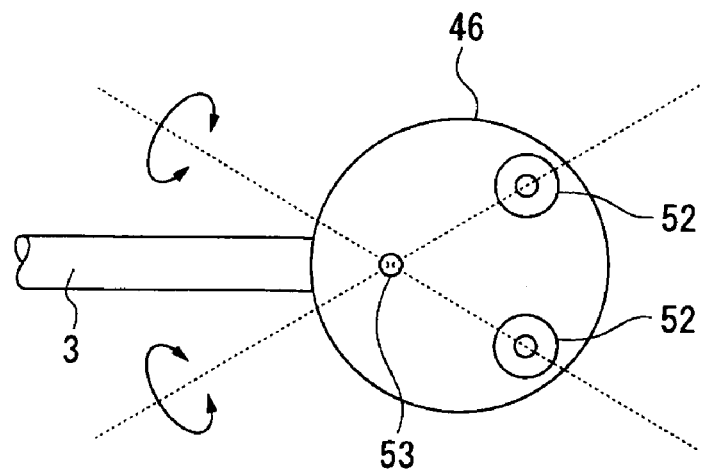
FIG. 11 is a schematic plan view showing a rough outline of another entrance side adjusting mechanism.
Figure 12:
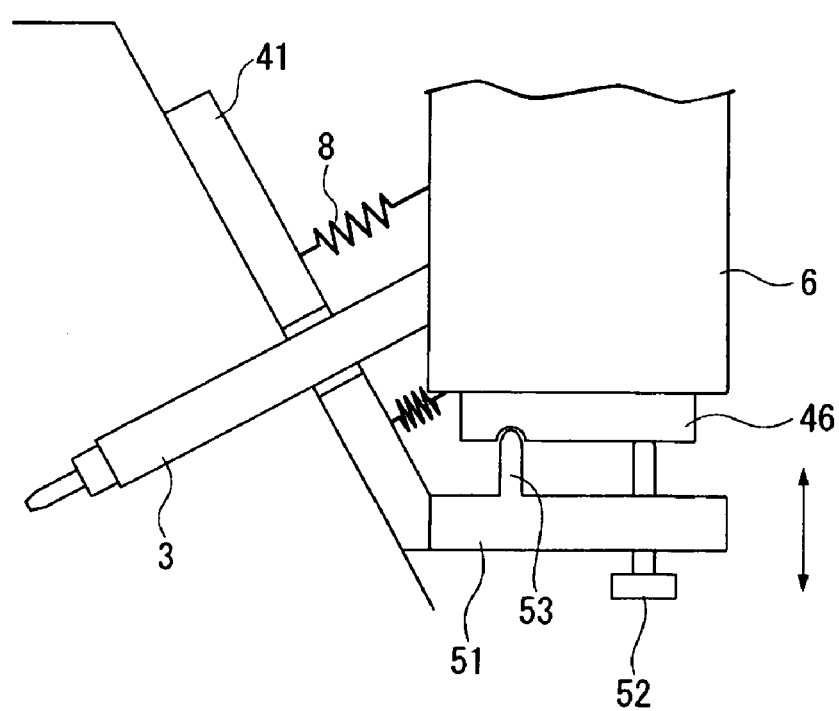
FIG. 12 is a schematic cross-sectional view of the entrance side adjusting mechanism shown in FIG. 11.
Figure 13:
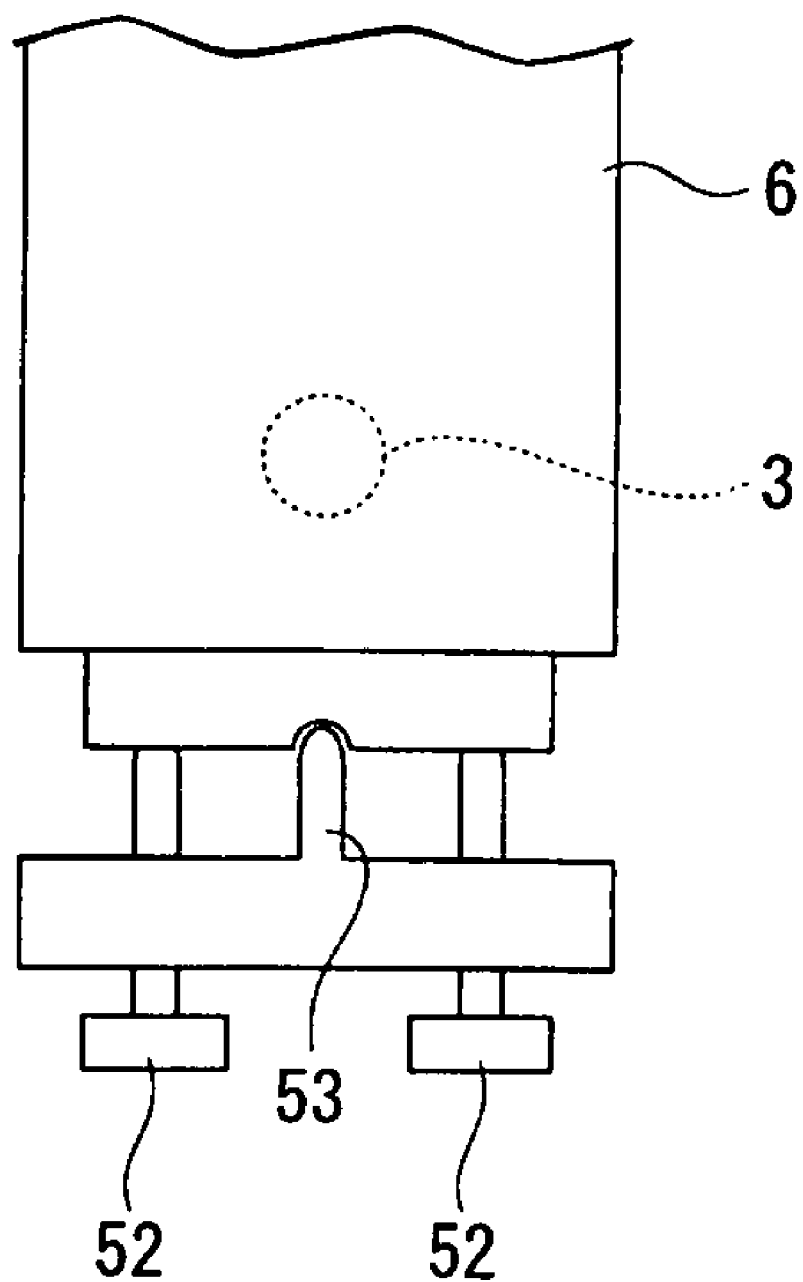
FIG. 13 is a schematic rear view of the entrance side adjusting mechanism shown in FIG. 11.

FIG. 11 is a schematic plan view showing a rough outline of another entrance side adjusting mechanism. FIG. 12 is a schematic cross-sectional view of the entrance side adjusting mechanism shown in FIG. 11. FIG. 13 is a schematic rear view of the entrance side adjusting mechanism shown in FIG. 11. As shown in these drawings, the supporting member 46 for supporting the refrigerator 6 is supported at three points via an adjusting plate 51 connected to the bracket 41. In other words, by using a supporting protrusion 53, which is formed substantially on the center axis of the snout 3 from a view point in the height direction, as a base point, and changing the heights of adjusting screws 52 formed on lines traversing the center axis of the snout 3, the position of the refrigerator 6 can be adjusted, thus the entrance side focal point of the X-ray lens 1 can be adjusted.

Figure 14:
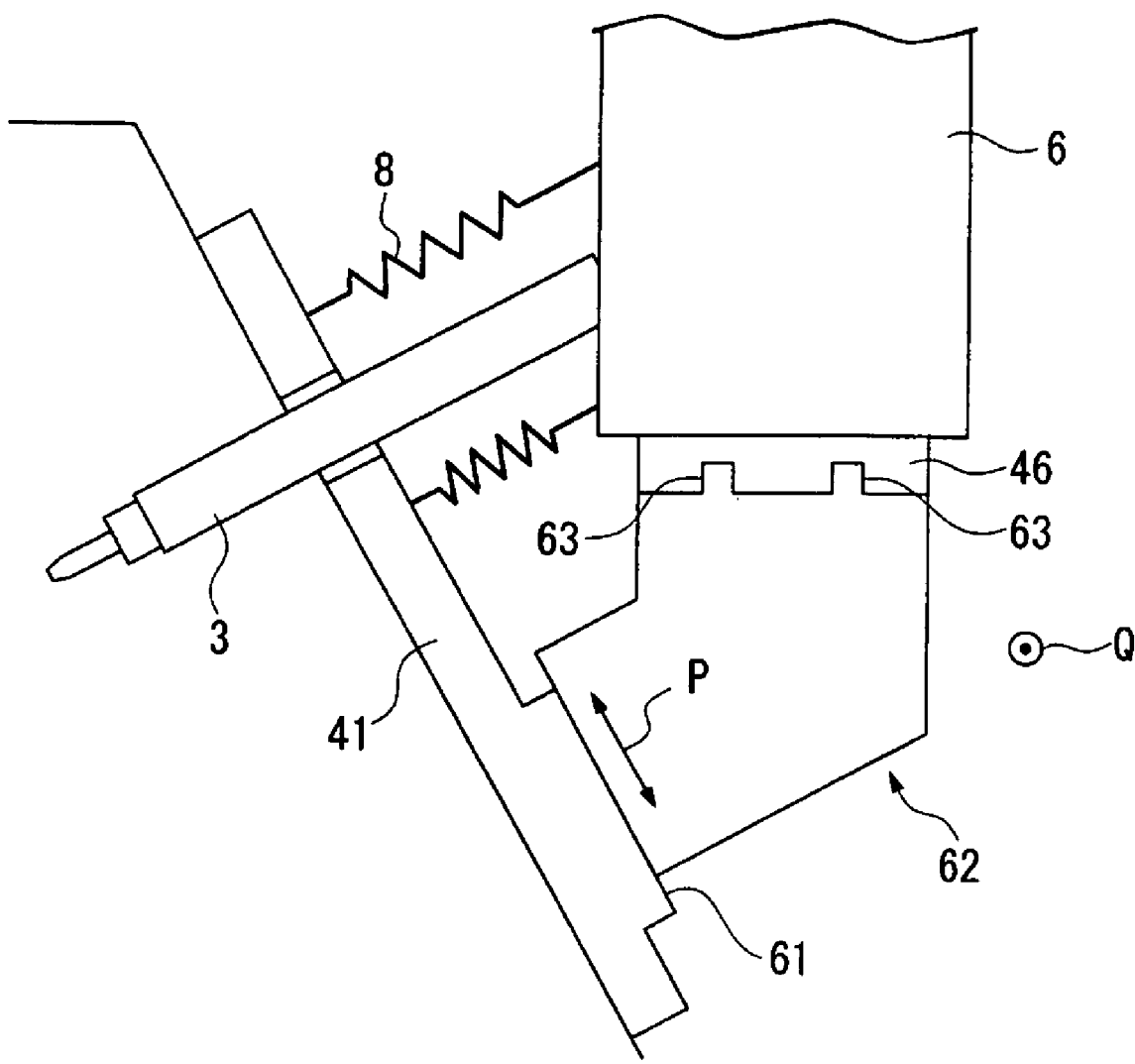
FIG. 14 is a schematic cross-sectional view showing a rough outline of still another entrance side adjusting mechanism.

FIG. 14 is a schematic cross-sectional view showing a rough outline of still another entrance side adjusting mechanism. As shown in the drawing, the supporting member 46 for supporting the refrigerator 6 and the bracket 41 are connected to each other via a sliding member 62. The sliding member 62 is formed to be able to slide as illustrated with the arrow P along a slide guide 61 provided to the bracket 41. Thus, with such movement of the sliding member 62, the refrigerator 6 coupled to the supporting member 46 can also slide as illustrated with the arrow P. Further, the supporting member 46 can slide along a sliding guide 63 provided to the sliding member 62 in directions of the arrow Q (the directions perpendicular to the sheet). By thus sliding the refrigerator 6 in the directions of arrows P and Q (either direction is substantially perpendicular to the optical axis of the X-ray lens 1), the entrance side focal point of the X-ray lens 1 connected to the refrigerator 6 can be adjusted in two directions perpendicular to the optical axis thereof.

Figure 15:
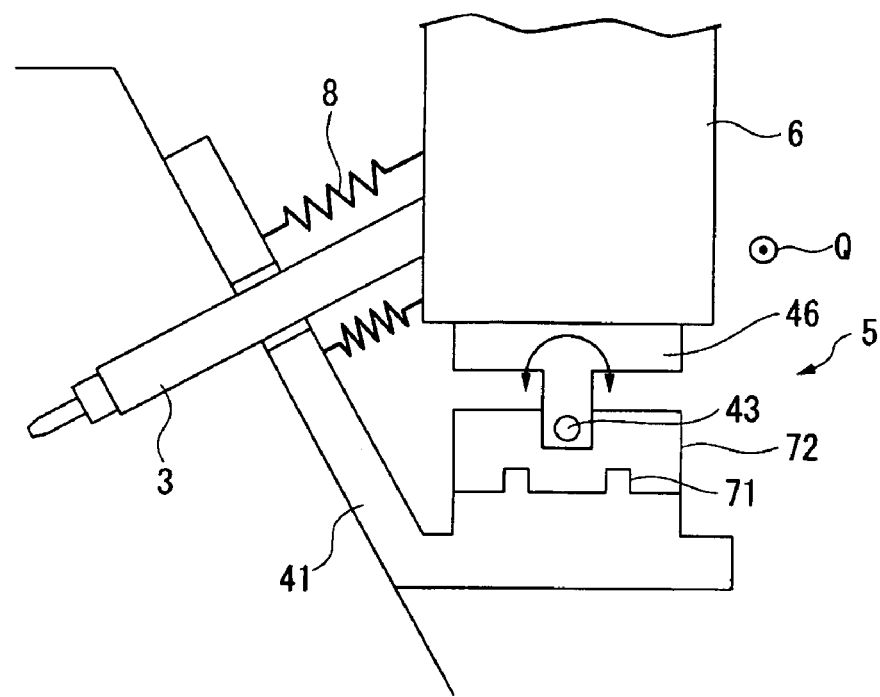
FIG. 15 is a schematic cross-sectional view showing a rough outline of still another entrance side adjusting mechanism.

FIG. 15 is a schematic cross-sectional view showing a rough outline of still another entrance side adjusting mechanism. As shown in the drawing, the supporting member 46 for supporting the refrigerator 6 and the bracket 41 are connected to each other via a sliding member 72. The sliding member 72 is formed to be able to slide as illustrated with the arrow Q along a slide guide 71 provided to the bracket 41. Thus, with such movement of the sliding member 72, the refrigerator 6 coupled to the supporting member 46 can also slide as illustrated with the arrow Q. Further, the sliding member 72 is pivotally connected to the supporting member 46 via the rotary shaft 43. Thus, the supporting member 46 can be pivoted around the rotary shaft 43 alternatively in forward and backward directions. Accordingly, similarly to other embodiments described above, by sliding or rotationally moving the refrigerator 6, the snout 3 integrally coupled to the refrigerator 6 and further the entrance side focal point of the X-ray lens 1 mounted on the tip potion of the snout 3 can be adjusted.

Figure 16:
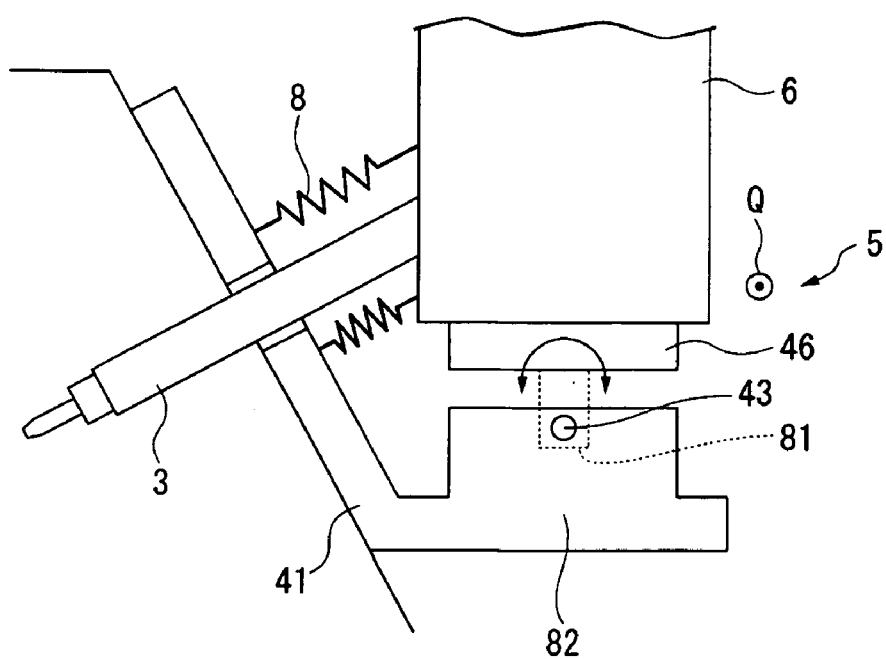
FIG. 16 is a schematic cross-sectional view showing a rough outline of still another entrance side adjusting mechanism.
Figure 17:
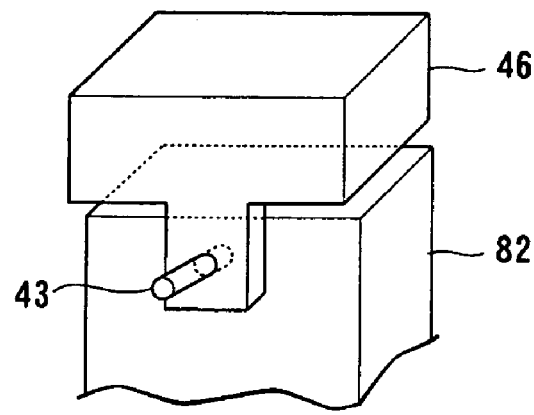
FIG. 17 is a cross-sectional view showing a substantial section of the entrance side adjusting mechanism shown in FIG. 16.
Figure 18:
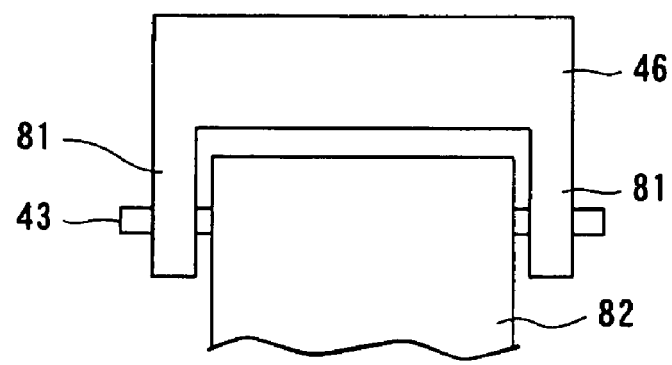
FIG. 18 is a cross-sectional view in the direction perpendicular to the direction of FIG. 16.

FIG. 16 is a schematic cross-sectional view showing a rough outline of still another entrance side adjusting mechanism. Further, FIG. 17 is a perspective view showing a substantial part of the entrance side adjusting mechanism shown in FIG. 16, and FIG. 18 is a cross-sectional view in the direction perpendicular to the direction of FIG. 16. As shown in these drawings, the supporting member 46 for supporting the refrigerator 6 and the bracket 41 are pivotally connected to each other via the rotary shaft 43. Thus, the supporting member 46 can be pivoted around the rotary shaft 43 alternatively in forward and backward directions. Further, in the present embodiment, as shown in FIG. 18, the rotary shaft 43 is pivotally mounted between protruding sections 81 extending below the supporting member 46 so as to pass through a receiving section 82. Therefore, the supporting member 46 can be shifted with respect to the receiving section 82 along the center axis direction (denoted by the arrow Q) of the rotary shaft 43. Accordingly, similarly to other embodiments described above, by sliding or rotationally moving the refrigerator 6, the snout 3 integrally coupled to the refrigerator 6 and further the entrance side focal point of the X-ray lens 1 mounted on the tip potion of the snout 3 can be adjusted.

Figure 19:
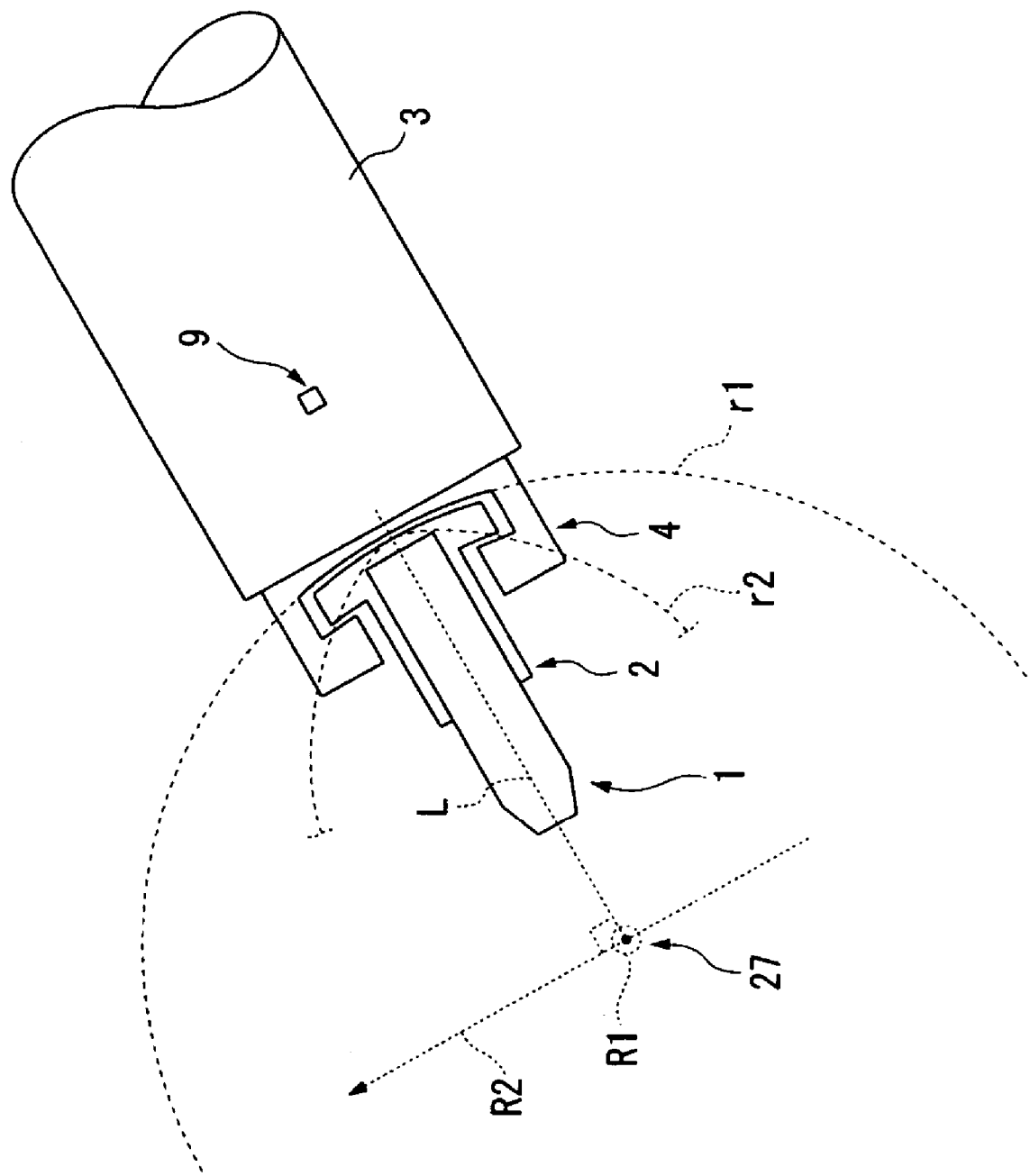
FIG. 19 is a schematic cross-sectional view showing a rough outline of another example of the exit side adjusting mechanism.

FIG. 19 is a schematic cross-sectional view showing a rough outline of another example of the exit side adjusting mechanism. In the exit side adjusting mechanism having the configuration shown in the drawing, the x-ray lens 1 is arranged to be able to rotationally move around two axes each passing through the entrance side focal point (the X-ray source 27 in this vessel) and perpendicular to the optical axis L. In other words, in the drawing, the axes R1 and R2 are both perpendicular to the optical axis L, and the axis R1 is arranged in the direction perpendicular to the sheet while the axis R2 is arranged in the same plane as the sheet, namely in the direction perpendicular to the axis R1. Accordingly, the X-ray lens 1 rotationally moves on a rotational locus r1, which is a circle within the same plane as the sheet, taking the axis R1 as the rotational axis. Further, the X-ray lens 1 rotationally moves on a rotational locus r2 (for the sake of convenience of illustration, a circular arc in an oblique plane is illustrated in FIG. 19), which is a circle within a plane perpendicular to the sheet, taking the axis R2 as the rotational axis. By thus arranging the configuration, the exit side focal point position can be adjusted without changing the entrance side focal point position. Note that it is obvious that the axes R1 and R2 are not limited to the above arrangement, provided the axes R1 and R2 are perpendicular to the optical axis L.

Although the content of the invention is explained with reference to the embodiments as described above, it is obvious that the content of the invention is not limited to the embodiments only. For example, although the case of the application to the superconducting X-ray detector is explained in the embodiments, the application is not so limited, but the application to other types of X-ray detectors such as an X-ray detector utilizing a silicon detector is also possible.

What is claimed is:

1. An optical axis adjusting mechanism for an X-ray lens to be implemented in an X-ray analytical instrument, comprising:
   an exit side adjusting mechanism for adjusting an exit side focal point of the X-ray lens to focus on an X-ray detector; and
   an entrance side adjusting mechanism for adjusting an entrance side focal point of the X-ray lens to focus on an analytical point of a sample,
   wherein the entrance side adjusting mechanism is disposed at a greater distance from the X-ray lens than a distance between the exit side adjusting mechanism and the X-ray lens.

2. The optical axis adjusting mechanism for an X-ray lens according to claim 1, wherein
   the exit side adjusting mechanism includes a mechanism capable of translating the X-ray lens in parallel with two directions perpendicular to the optical axis of the X-ray lens.

3. The optical axis adjusting mechanism for an X-ray lens according to claim 2, wherein
   the exit side adjusting mechanism includes a detachable section configured to allow at least a portion operated by an operator to be detached.

4. The optical axis adjusting mechanism for an X-ray lens according to claim 1, wherein
   the exit side adjusting mechanism includes a mechanism capable of rotationally moving the X-ray lens around two axes passing through the entrance side focal point of the X-ray lens and perpendicular to the optical axis of the X-ray lens.

5. The optical axis adjusting mechanism for an X-ray lens according to claim 3, wherein
   the exit side adjusting mechanism includes a detachable section configured to allow at least a portion operated by an operator to be detached.

6. The optical axis adjusting mechanism for an X-ray lens according to claim 1, wherein
   the X-ray lens includes a holding mechanism for keeping the X-ray lens in a position adjusted by the exit side adjusting mechanism.

7. The optical axis adjusting mechanism for an X-ray lens according to claim 1, wherein
   the X-ray detector is a superconducting X-ray detector mounted on a refrigerator,
   the entrance side adjusting mechanism is disposed adjacent to the refrigerator, and
   the exit side adjusting mechanism is movable integrally with the refrigerator.

8. The optical axis adjusting mechanism for an X-ray lens according to claim 7, wherein
   the entrance side adjusting mechanism includes a mechanism capable of translating the refrigerator in parallel with two directions traversing the optical axis of the X-ray lens.

9. The optical axis adjusting mechanism for an X-ray lens according to claim 8, wherein
   the two directions are substantially perpendicular to the optical axis of the X-ray lens.

10. The optical axis adjusting mechanism for an X-ray lens according to claim 7, wherein
    the entrance side adjusting mechanism includes a mechanism capable of translating the refrigerator in parallel with a horizontal direction perpendicular to the optical axis of the X-ray lens.

11. The optical axis adjusting mechanism for an X-ray lens according to claim 7, wherein
    the entrance side adjusting mechanism includes a mechanism capable of rotationally moving the refrigerator around each of two axes positioned differently from the optical axis of the X-ray lens and passing through one of the refrigerator and an area adjacent to the refrigerator.

12. The optical axis adjusting mechanism for an X-ray lens according to claim 7, wherein
    the entrance side adjusting mechanism includes:
    a mechanism capable of rotationally moving the refrigerator around a rotational axis positioned differently from the optical axis of the X-ray lens and passing through one of the refrigerator and an area adjacent to the refrigerator; and
    the rotational axis of the mechanism rotationally moving the refrigerator is substantially perpendicular to the ground.

13. The optical axis adjusting mechanism for an X-ray lens according to claim 12, wherein
    the entrance side adjusting mechanism moves the entrance side focal point of the X-ray lens approximately parallel to a direction substantially perpendicular to the optical axis of the X-ray lens by the rotational movement around the rotational axis.

14. The optical axis adjusting mechanism for an X-ray lens according to claim 12, wherein
    the entrance side adjusting mechanism includes a mechanism capable of moving the entrance side focal point of the X-ray lens integrally with the refrigerator in a horizontal direction.

15. The optical axis adjusting mechanism for an X-ray lens according to claim 7, wherein
    the entrance side adjusting mechanism includes:
    a mechanism capable of translating the entrance side focal point of the X-ray lens integrally with the refrigerator in parallel with a direction traversing the optical axis of the X-ray lens; and
    a mechanism capable of rotationally moving the entrance side focal point of the X-ray lens integrally with the refrigerator around an axis positioned differently from the optical axis of the X-ray lens.

16. The optical axis adjusting mechanism for an X-ray lens according to claim 7, wherein
    the entrance side adjusting mechanism is capable of adjusting the entrance side focal point of the X-ray lens, while firmly connecting a stage mounting the entrance side adjusting mechanism thereon with an analytical vessel containing the sample, an excitation source and a detector, and then inserting the X-ray lens in the analytical vessel.

17. The optical axis adjusting mechanism for an X-ray lens according to claim 7, wherein
the entrance side adjusting mechanism is capable of adjusting the entrance side focal point of the X-ray lens, while connecting the refrigerator with a scanning electron microscope via a bellows, and firmly connecting a stage mounting the entrance side adjusting mechanism thereon to the scanning electron microscope, and then inserting the X-ray lens in a vacuum vessel of the scanning electron microscope.

18. An X-ray analytical instrument comprising the optical axis adjusting mechanism according to claim 1.

19. A method of adjusting an optical axis of an X-ray lens to be implemented in an X-ray analytical instrument, comprising:

disposing an entrance side adjusting mechanism for adjusting an entrance side focal point of the X-ray lens to focus on an analytical point of a sample at a greater distance from the X-ray lens than a distance between an exit side adjusting mechanism for adjusting an exit side focal point of the X-ray lens to focus on an X-ray detector and the X-ray lens;

adjusting the exit side focal point of the X-ray lens to focus on the X-ray detector by the exit side adjusting mechanism; and adjusting the entrance side focal point of the X-ray lens to focus on the analytical point of the sample by the entrance side adjusting mechanism.

* * * * *